United States Patent [19]

Duckwall, Jr.

[11] 4,405,819

[45] Sep. 20, 1983

[54] PROCESS FOR THE PRODUCTION OF ALCOHOLS FROM CARBOXYLIC ACIDS

[75] Inventor: Louis R. Duckwall, Jr., Ponca City, Okla.

[73] Assignee: Conoco Inc., Ponca City, Okla.

[21] Appl. No.: 374,212

[22] Filed: May 3, 1982

[51] Int. Cl.$^3$ .............................................. C07C 29/00
[52] U.S. Cl. .................................. 568/814; 568/861; 568/864
[58] Field of Search ................ 568/814, 852, 861, 864

[56] References Cited

U.S. PATENT DOCUMENTS

| | | | |
|---|---|---|---|
| 1,839,974 | 1/1932 | Lazibb et al. | 568/814 |
| 2,965,660 | 12/1960 | Heise et al. | 562/405 |
| 3,524,892 | 8/1970 | Horlenku et al. | 568/864 |
| 4,032,458 | 6/1977 | Cooley et al. | 568/864 |
| 4,087,470 | 5/1978 | Suzuk | 568/864 |
| 4,252,688 | 2/1981 | Gallei et al. | 252/455 Z |
| 4,346,240 | 8/1982 | Grey et al. | 568/864 |

FOREIGN PATENT DOCUMENTS

| | | | |
|---|---|---|---|
| 50-2490 | 1/1975 | Japan | 568/864 |
| 783661 | 11/1957 | United Kingdom | 568/814 |

Primary Examiner—Werren B. Lone
Attorney, Agent, or Firm—Cortlan R. Schupbach, Jr.

[57] ABSTRACT

An improved process is provided for the production of alcohols from carboxylic acids using the reaction of carboxylic acids with alcohols in the presence of hydrogen and carbon monoxide to form esters which are subsequently hydrogenated over a suitable hydrogenation catalyst. The invention is useful because the temperature and pressure conditions are reduced from current commercial processes while hydrogenation catalyst activity and lifetime are promoted by the removal of catalyst poisons such as water.

7 Claims, 1 Drawing Figure

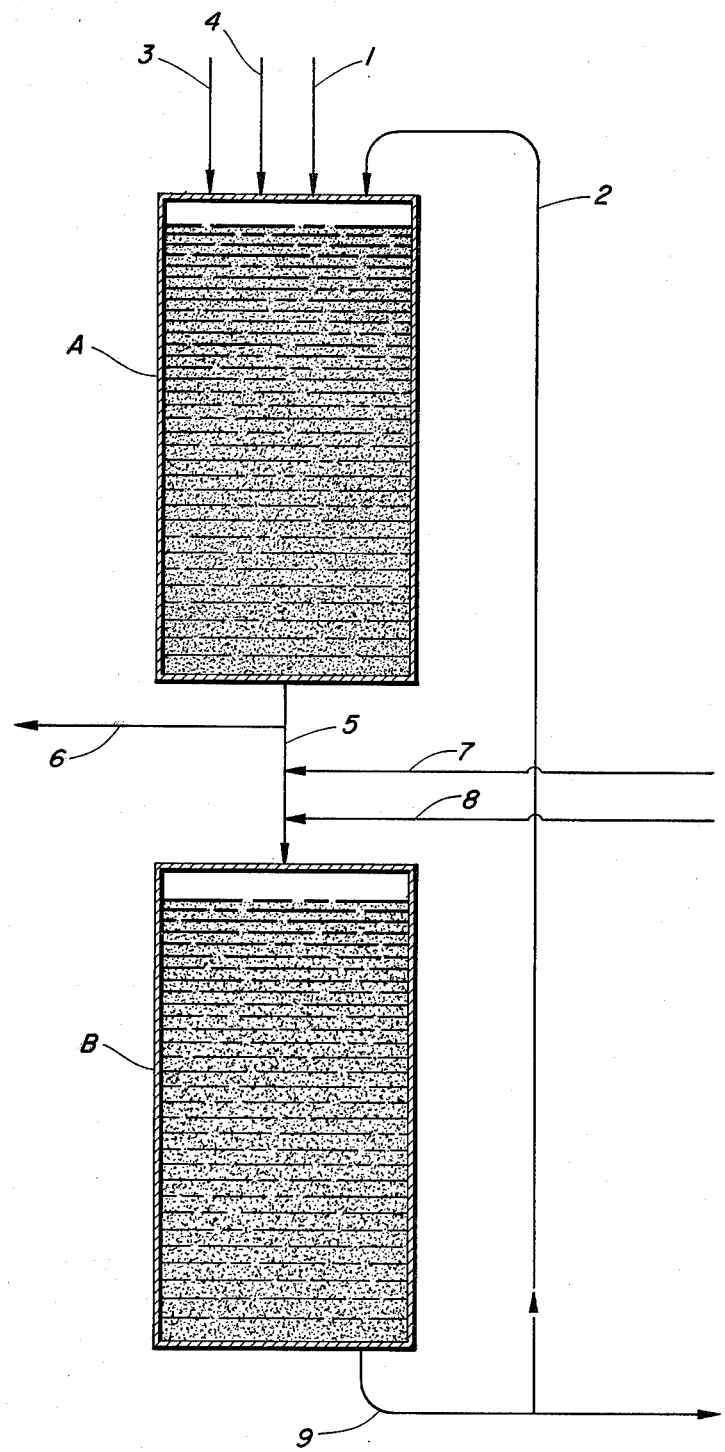

PROCESS FOR THE PRODUCTION OF ALCOHOLS FROM CARBOXYLIC ACIDS

This invention relates to a process for the production of alcohols from carboxylic acids. More specifically, this invention relates to a process for a conversion of carboxylic acids to carboxylic acid esters and the subsequent catalytic hydrogenation of these carboxylic acid esters to the corresponding alcohols. In addition the invention provides for the reduction of catalyst poisons through the use of carbon monoxide.

Some of the most important commercial alcohols are fatty alcohols obtained from natural sources. Producing these alcohols from carboxylic acids is very difficult because the reaction requires hazardous conditions of high pressure hydrogen and high reaction temperatures. Since demand for these alcohols has outstripped the natural supply, various means of producing these alcohols synthetically have been practiced.

The production of such alcohols is described in the literature in U.S. Pat. No. 1,839,974 which teaches a method for the direct catalytic reduction of carboxylic acids. This method depends upon the use of hydrogen for the removal of oxygen from the acid function in the form of water while still another molecule of hydrogen takes up the position of the oxygen atom removed. Thereafter, an esterification reaction occurs between a portion of the alcohol formed with a portion of the remaining acid. The hydrogenation catalyst is rapidly deactivated by the large amounts of acid present and this method produces water which is a catalyst poison and is known to have detrimental effects.

U.S. Pat. No. 2,965,660 teaches a process for the catalytic production of carboxylic acid esters by reduction of organic carboxylic acids using carbon monoxide or mixtures containing largely carbon monoxide in admixture with hydrogen. However, this process produces a "scatter" or broad range of organic materials because of the uncontrollability of the reaction. Therefore, materials other than the desired alcohols for any particular use are also produced and must be separated. British Pat. No. 783661 teaches producing fatty acid esters in the presence of a mixture of hydrogen and carbon monoxide using copper/chromium oxide as the catalyst. This reference teaches carbon monoxide as a poison and states the method taught to be effective in spite of the presence of carbon monoxide. Methanol is produced using the method.

The recognition of water as a catalyst poison is set forth in *Chemical Abstracts* 110746s, which teaches the use of an inert sweep gas to physically remove water from the high pressure hydrogenation of fatty acid esters. Further, the *Journal of Catalysis*, volume 5, 1966, pages 401 through 411 also teaches that water is a catalyst poison. In this reference it is proposed that carbon monoxide is produced by decomposition of methanol during the heating process and in turn promotes the catalyst. The reference teaches that in such a process water is surprisingly not a detriment.

These references are representative but non-exhaustive of the prior art which teaches in large part that carboxylic acid esters can be utilized to produce alcohols. However, as indicated by these references, the processes are detrimental in many respects including low catalyst activity, rapid catalyst degradation, high pressures and temperatures necessary to carry out the processes and uncontrollability of the products achieved. It would therefore be of great benefit to provide a process which is simple, requires more moderate conditions and produces alcohols of highly controllable molecular weight.

It has now been discovered in accordance with the present invention that alcohols can be produced from carboxylic acids utilizing a continuous catalyst-free acid process which comprises combining carboxylic acids with an alcohol in the presence of carbon monoxide to produce carboxylic acid esters and carbon dioxide, then combining the carboxylic acid esters so obtained with hydrogen and carbon monoxide over a standard hydrogenation catalyst to obtain alcohols of desired molecular weight.

The instant invention thus has many advantages over the prior art methods. No catalyst is utilized other than a standard hydrogenation catalyst. If desired, alcohol utilized to react with the carboxylic acids can be obtained directly from the product stream, thus tightly controlling the type of alcohols obtained. The use of hydrogen and carbon monoxide effectively removes water from the reaction, thereby eliminating side reactions and catalyst deactivation.

Catalyst life is additionally enhanced since acid does not contact the catalyst. Acid processes heretofore known suffered catalyst loss from degradation by the fatty acid feed. The instant invention avoids contact between the fatty acids and the hydrogenation catalyst. Water is chemically removed before contacting the catalyst to further extend catalyst life.

Thus in the first stage of the present invention carboxylic acids are combined with alcohols in the presence of carbon monoxide to produce carboxylic acid esters. The reaction proceeds by the continuous removal of water and the process is effective for both continuous and batch process applications. This invention is a distinct improvement to the prior art methods wherein acid or base catalysts are used at some point in the production of such carboxylic acid esters, followed by some method of neutralization or purification. U.S. Pat. No. 2,965,660 teaches a similar method but requires a catalyst, does not utilize alcohols as a feed and produces a "scatter" of products in contrast to the controlled process of the present invention. The present invention produces carboxylic acid esters without a catalyst in high yield with minimal handling or purification.

Once obtained, the carboxylic acid esters are hydrogenated to alcohols in high yield in either a continuous or batch process using reduced reaction conditions and a hydrogen feed gas containing carbon monoxide. This process is in distinct contrast to the well known acid methyl ester batchwise process which requires purification prior to hydrogenation. A second commercial process which is improved upon by the present invention involves combining a slurry feed of carboxylic acid, powdered catalyst and a large excess of an alcohol with a hydrogen feed gas and batch-type reactor.

Carboxylic acid starting materials of the present invention can be any acid capable of esterification and subsequent hydrogenation. In general, these acids have the general formula RCOOH wherein R is normally a branched or unbranched, saturated or unsaturated aliphatic group containing from 1 to about 28 carbon atoms. However, R can also be aromatic and can contain additional organic acid groups as exemplified by adipic acid, all of which will be esterified and subsequently reduced.

Representative but non-exhaustive examples of carboxylic acids useful in the practice of the present invention are

| | | |
|---|---|---|
| $C_5H_{11}COOH$ | $C_{17}H_{29}COOH$ | $HOOC-CH_2-COOH$ |
| $C_6H_{13}COOH$ | $C_{18}H_{37}COOH$ | $HOOC-CH_2CH_2-COOH$ |
| $C_7H_{15}COOH$ | $C_{19}H_{39}COOH$ | $HOOC-CH_2CH_2CH_2-COOH$ |
| $C_8H_{17}COOH$ | $C_{19}H_{37}COOH$ | $HOOC-(CH_2)_4COOH$ |
| $C_9H_{19}COOH$ | $C_{19}H_{35}COOH$ | $HOOC-(CH_2)_5COOH$ |
| $C_{10}H_{21}COOH$ | $C_{19}H_{33}COOH$ | $HOOC-(CH_2)_6COOH$ |
| $C_{11}H_{23}COOH$ | $C_{19}H_{31}COOH$ | $HOOC-(CH_2)_7COOH$ |
| $C_{12}H_{25}COOH$ | $C_{19}H_{29}COOH$ | $HOOC-(CH_2)_8COOH$ |
| $C_{13}H_{27}COOH$ | $C_{20}H_{41}COOH$ | R–⟨O⟩–COOH |
| $C_{13}H_{25}COOH$ | $C_{21}H_{43}COOH$ | |
| $C_{14}H_{29}COOH$ | $C_{21}H_{41}COOH$ | |
| $C_{15}H_{31}COOH$ | $C_{21}H_{39}COOH$ | R–⟨O⟩(COOH)(COOH) |
| $C_{15}H_{29}COOH$ | $C_{21}H_{37}COOH$ | |
| $C_{16}H_{33}COOH$ | $C_{21}H_{35}COOH$ | (COOH,COOH,COOH)$_n$ |
| $C_{16}H_{35}COOH$ | $C_{21}H_{33}COOH$ | |
| $C_{17}H_{33}COOH$ | $C_{22}H_{45}COOH$ | poly(acrylic acids) where n is the number of repetitive units, normally from about 10 to about 100,000, preferably 10 to about 1,000. |
| $C_{17}H_{31}COOH$ | $C_{23}H_{47}COOH$ | |

The alcohol for the initial reaction of carbon monoxide with carboxylic acid to produce the carboxylic acid ester has the general formula $R_2OH$ wherein $R_2$ is normally an alkyl group containing from 1 to 30 carbon atoms. These alkyl groups may be linear or branched, and may contain one or more aromatic, or alcohol functions. These alcohols are most conveniently the product alcohols of the process, a small portion of which is utilized in the reaction with carboxylic acids.

Representative but non-exhaustive examples of alcohols useful in this invention are

| | | |
|---|---|---|
| $C_5H_{11}CH_2OH$ | $C_{21}H_{43}CH_2OH$ | R–⟨O⟩–CH$_2$OH |
| $C_6H_{13}CH_2OH$ | $C_{21}H_{41}CH_2OH$ | |
| $C_7H_{15}CH_2OH$ | $C_{21}H_{39}CH_2OH$ | R–⟨O⟩(CH$_2$OH)(CH$_2$OH) |
| $C_8H_{17}CH_2OH$ | $C_{21}H_{37}CH_2OH$ | |
| $C_9H_{19}CH_2OH$ | $C_{21}H_{35}CH_2OH$ | |
| $C_{10}H_{21}CH_2OH$ | $C_{21}H_{33}CH_2OH$ | (CH$_2$OH,CH$_2$OH,CH$_2$OH)$_n$ |
| $C_{11}H_{23}CH_2OH$ | $C_{22}H_{45}CH_2OH$ | |
| $C_{12}H_{25}CH_2OH$ | $C_{23}H_{47}CH_2OH$ | poly(alkyl alcohol) where n is number of repetitive units normally from about 1 to about 10,000 preferably from 10 to 1,000. |
| $C_{13}H_{27}CH_2OH$ | | |
| $C_{13}H_{25}CH_2OH$ | $HOCH_2CH_2OH$ | |
| $C_{14}H_{29}CH_2OH$ | $HOCH_2CH_2CH_2OH$ | |
| $C_{15}H_{31}CH_2OH$ | $HO(CH_2)_4OH$ | |
| $C_{15}H_{29}CH_2OH$ | $HO(CH_2)_5OH$ | |
| $C_{16}H_{35}CH_2OH$ | $HO(CH_2)_6OH$ | |
| $C_{17}H_{35}CH_2OH$ | $HO(CH_2)_7OH$ | |
| $C_{17}H_{33}CH_2OH$ | $HO(CH_2)_9OH$ | |
| $C_{17}H_{31}CH_2OH$ | $HO(CH_2)_{10}OH$ | |
| $C_{17}H_{29}CH_2OH$ | | |
| $C_{18}H_{37}CH_2OH$ | CH$_2$OH–CH$_2$OH (branched) | $HO(CH_2CH_2O)_{\overline{n}}H$ ethylene glycols wherein n is the number of repetitive units, normally from 1 to about 100, preferably 1 to about 30 |
| $C_{19}H_{39}CH_2OH$ | | |
| $C_{19}H_{37}CH_2OH$ | | |
| $C_{19}H_{35}CH_2OH$ | | |
| $C_{19}H_{33}CH_2OH$ | | |
| $C_{19}H_{31}CH_2OH$ | | |
| $C_{19}H_{29}CH_2OH$ | | |
| $C_{20}H_{41}CH_2OH$ | | |

The combination of carboxylic acids with alcohols is normally carried out at temperatures of from about 200° C. to about 400° C. The invention is operable at lower temperatures than prior art processes but can, if desired for any reason, be carried out at these higher temperatures. This reaction can be carried out at a pressure of from 1 to 350 atmospheres but normally a pressure of from about 50 to about 300 atmospheres will be used.

The hydrogenation of the resultant carboxylic acid ester is normally carried out over hydrogenation catalysts well known to those skilled in this art. In general, hydrogenation catalysts include both metallic and metallic oxide compounds of transition elements in sub-group I such as copper, sub-group II such as zinc, sub-group VI such as chromium, sub-group VII such as manganese, and sub-group VIII such as iron. Support materials such as bentonite, Fuller's Earth, activated charcoal alumina and the like can be used. Representative but non-exhaustive examples of such catalysts are Cu-Fe-Al as described in U.S. Pat. No. 4,252,689, zinc chromate, copper chromite, Raney nickel, and copper chromite promoted by manganese. However, of these catalysts the most commonly encountered and most preferred is copper chromite.

The hydrogenation step is normally carried out at temperatures of from about 200° to about 350° C., although temperatures of about 300° C. are preferred. The hydrogenation is normally carried out at pressures of from about 100 to about 300 atmospheres, although pressures of from about 150 to about 250 atmospheres are preferred, in contrast to the 300 atmospheres and more used in prior commercial processes.

GENERAL DESCRIPTION OF THE DRAWING

The FIGURE is a graphic representation of the process of the present invention showing the reaction of carboxylic acids with alcohols to produce carboxylic acid esters, which are then hydrogenated to product alcohols.

DETAILED DESCRIPTION OF THE INVENTION

The sole FIGURE is a description of the process of the present invention wherein carboxylic acids are fed to a first stage (A) through line 1 together with product alcohols through line 2. In addition, the reactor is supplied with hydrogen and carbon monoxide through lines 3 and 4. Reactor (A) contains a finely divided support material to increase the surface available to the reaction which is carried out solely under conditions of temperature and pressure in the absence of a catalyst. Examples of such inert support materials which are used include glass beads, wash sand and the like.

In Reactor (A) organic acids are converted to organic acid esters and carbon dioxide, which exit the reactor through line 5. Carbon dioxide can be removed via line 6 and the organic acid esters proceed into reactor (B) which contains a hydrogenation catalyst of choice (preferably but not critically copper chromite in a fixed bed). The reactor is additionally supplied through lines 7 and 8 with additional hydrogen and carbon monoxide. The organic acid esters are hydrogenated to organic alcohols of the desired molecular weight range and exit the reactor through product line 9, from which slip stream line 2 is diverted for recycle to the reactor step (A).

The reaction which occurs in reactor (B) produces extremely high quality alcohols in high yield.

The reaction produces $CO_2$, which can be disposed of with unreacted hydrogen feed gas. However, if hydrogen feed gas is recycled, unwanted $CO_2$ product is preferably continuously removed from the feed gas stream. $CO_2$ can be removed by means well known to those skilled in this art, such as by $CO_2$ scrubbers.

The instant invention is more concretely described with reference to the examples below wherein all parts and percentages are by weight unless otherwise specified. The examples are provided to illustrate the instant invention and not to limit it.

Examples 1 and 2 illustrate the first step of the process for the formation of carboxylic acid esters.

EXAMPLE 1

In a batch process a 2-liter stainless steel autoclave with stirrer was equipped with a gas bubbling device and a back-pressure regulator for gas flow control. The autoclave was charged with 350 grams (1.75 mole) of dodecanoic acid and 325.5 grams (1.75 mole) of dodecanol. The autoclave was evacuated and refilled with feed gas. The The autoclave was heated to 150° C. with agitation and an approximately 2 to 1 mixture of hydrogen to carbon monoxide was bubbled through the reaction mixture at a set pressure of 1000 psig. These conditions were maintained for 3 hours. The autoclave conditions were then reduced to ambient temperature and pressure. Pure carboxylic acid ester was thereafter ready for hydrogenation.

EXAMPLE 2

In a continuous process, a liquid feed consisting of 1:1 molar ratio mixture of dodecanoic acid and dodecanol is pumped into a glass bead packed stainless steel tubular reactor equipped with a backpressure regulator. The gaseous feed consisting of a 2:1 mixture of hydrogen and carbon monoxide is concurrently introduced into the reactor. The temperature and pressure of the reactor are maintained at 150° C. and 1000 psig respectively, and the liquid hourly space velocity of these conditions is maintained at 0.5. The pure carboxylic acid ester produced is ready for use as hydrogenation feed.

Catalytic hydrogenation of the carboxylic acid esters thus obtained is improved by using a hydrogen feed gas containing carbon monoxide and is illustrated in Example 3 for a batch process and in Example 4 for a continuous process.

EXAMPLE 3

A 2-liter stainless steel autoclave with stirrer is charged with 675.5 grams (1.75 mole) of dodecyl dodecanoate and 14.0 grams (2% by weight) of copper chromite hydrogenation catalyst. The autoclave is sealed, evacuated, and sparged with nitrogen at 100° C. A gaseous mixture of hydrogen and carbon monoxide in a ratio of 2:1 at a pressure of 500 psig is set on the autoclave while the temperature of the reaction is raised to 270° C. The feed gas pressure is then raised to 3000 psig and after 30 minutes at these conditions, the autoclave is cooled at ambient temperature and pressure is relieved. A typical example after several preparations with the same catalyst shows greater than 96% conversion of ester to alcohol.

EXAMPLE 4

A stainless steel tubular reactor is packed with a fixed bed of copper chromite hydrogenation catalyst and filled with carboxylic acid ester feed. Concurrent with the carboxylic acid ester liquid feed a gaseous mixture of hydrogen and carbon monoxide in the ratio of about 2:1 is bubbled through the reactor. The temperature and pressure of the reactor are gradually raised to 270° C. and 3000 psig over a period of 1 hour and maintained at these conditions for the balance of the run. The liquid hourly space velocity of the liquid feed is maintained at 0.5 under these conditions and a typical example of product shows 92 to 96% conversion of ester to alcohol.

It has been discovered that copper chromite catalysts when used for hydrogenation can be extended in life by maintaining the addition of carbon monoxide throughout the bed as is illustrated in Example 4.

When carried out continuously, the process of the instant invention is normally carried out at a liquid hourly space velocity (LHSV) of from about 0.1 to about 10. However, more commonly, LHSV of from about 0.3 to about 2 will be used and most preferred are LHSV of 0.3 to 1.0.

Although exemplified as separate stage reactors in the previous examples, the instant invention is especially situated to a 2-stage single reactor process as illustrated in Examples 5 and 6.

EXAMPLE 5

In a batch reaction a 2-liter stainless steel autoclave with stirrer is equipped with a gas bubbling device and a back-pressure regulator for gas flow control. The autoclave was charged with 350 grams (1.75 mole) of dodecanoic acid, 325.5 grams (1.75 mole) of dodecanol, and 14.0 gram (approximately 2% by weight) copper chromite hydrogenation catalyst. The autoclave is sealed, evacuated, and sparged with nitrogen at 100° C. Stirring is begun. A 2:1 mixture of hydrogen and carbon monoxide respectively is bubbled through the reaction mixture at a set pressure of 1000 psig. The temperature and pressure of the reaction are raised gradually to 270° C. and 3000 psig respectively over a 3 hour minute period. The conditions are maintained for 1 hour. The autoclave conditions are then reduced to ambient temperature and pressure. A typical sample after several preparations with the same catalyst will show that 92 to 96% conversion of acid to alcohol has occurred.

EXAMPLE 6

The first half of the stainless steel tubular reactor is packed with glass beads while the remainder of the reactor is packed with copper chromite hydrogenation catalyst. To initiate reaction the reactor is filled with a carboxylic acid ester liquid feed. To the same point of entry as the liquid feed a gaseous mixture of hydrogen and carbon monoxide in the ratio of 2:1 is bubbled through the reactor. The temperature of the first half of the reactor is raised gradually to 300° C. while the temperature of the second half of the reactor is raised gradually to 270° C. The entire reactor is maintained at a pressure of 3000 psig. The reaction conditions are reached gradually over a period of 1 hour. After reaction conditions are reached the liquid feed is changed to a 1 to 1.1 mixture of carboxylic acid and an alcohol respectively. The (LHSV) of the liquid feed is maintained at 0.5 under these conditions. A typical sample of product will show a 92 to 96% conversion of acid to alcohol.

Thus it is apparent that the instant invention provides a simple mild reaction condition process for the conversion of organic acids to alcohols while maintaining molecular weight control. The reaction likewise is a simple easily carried out process which produces alcohols of high purity.

While certain embodiments and details have been shown for the purpose of illustrating this invention, it will be apparent to those skilled in this art that various changes and modifications may be made herein without departing from the spirit or scope of the invention.

I claim:

1. An improved continuous fixed bed acid process for the production of alcohols from carboxylic acids in high yields comprising (a) reacting at a temperature of from about 100° C. to about 400° C. and a pressure of from about 1 atmosphere to about 350 atmospheres, carboxylic acids having the general formula RCOOH, wherein R is an alkyl group containing from 1 to 24 carbon atoms and which can contain additional organic acid groups, with alcohols having the general formula $R^2OH$, wherein $R^2$ is a linear or branched alkyl containing from 1 to 30 carbon atoms, to produce carboxylic acid esters, then hydrogenating the carboxylic acid esters at a temperature of from about 200° C. to about 350° C. and a pressure of from about 100 atmospheres to about 350 atmospheres with hydrogen and carbon monoxide over a hydrogenation catalyst selected from the group consisting of metallic and metallic oxide compounds of transition elements in subgroup I, subgroup II, subgroup V, subgroup VI and subgroup VIII of the Periodic Table to produce product alcohols, the improvement comprising adding a mixture of hydrogen and carbon monoxide as a sweep gas to the ester formation reaction.

2. A method as described in claim 1 wherein the volume ratio of hydrogen to carbon monoxide is about 2:1 respectively.

3. A method as described in claim 2 when carried out in a continuous fashion.

4. A method as described in claim 3 when carried out at a liquid hourly space velocity of from about 0.1 to about 10.0.

5. A method as described in claim 4 wherein the carboxylic acid is selected from the group consisting of

| | | |
|---|---|---|
| $C_5H_{11}COOH$ | $C_{17}H_{29}COOH$ | $HOOC-CH_2-COOH$ |
| $C_6H_{13}COOH$ | $C_{18}H_{37}COOH$ | $HOOC-CH_2CH_2-COOH$ |
| $C_7H_{15}COOH$ | $C_{19}H_{39}COOH$ | $HOOC-CH_2CH_2CH_2-COOH$ |
| $C_8H_{17}COOH$ | $C_{19}H_{37}COOH$ | $HOOC-(CH_2)_4COOH$ |
| $C_9H_{19}COOH$ | $C_{19}H_{35}COOH$ | $HOOC-(CH_2)_5COOH$ |
| $C_{10}H_{21}COOH$ | $C_{19}H_{33}COOH$ | $HOOC-(CH_2)_6COOH$ |
| $C_{11}H_{23}COOH$ | $C_{19}H_{31}COOH$ | $HOOC-(CH_2)_7COOH$ |
| $C_{12}H_{25}COOH$ | $C_{19}H_{29}COOH$ | $HOOC-(CH_2)_8COOH$ |
| $C_{13}H_{27}COOH$ | $C_{20}H_{41}COOH$ | 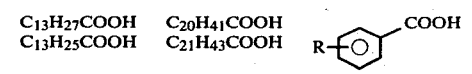 |
| $C_{13}H_{25}COOH$ | $C_{21}H_{43}COOH$ | |
| $C_{14}H_{29}COOH$ | $C_{21}H_{41}COOH$ | |
| $C_{15}H_{31}COOH$ | $C_{21}H_{39}COOH$ | 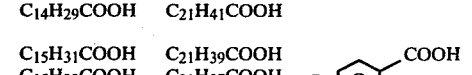 |
| $C_{15}H_{29}COOH$ | $C_{21}H_{37}COOH$ | |
| $C_{16}H_{33}COOH$ | $C_{21}H_{35}COOH$ | 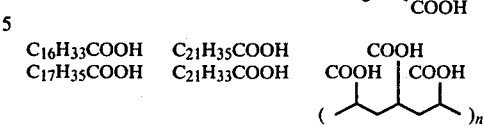 |
| $C_{17}H_{35}COOH$ | $C_{21}H_{33}COOH$ | |
| $C_{17}H_{33}COOH$ | $C_{22}H_{45}COOH$ | poly(acrylic acids) where n is the number of repetitive units, normally from about 10 to about 100,000, preferably 10 to about 1,000. |
| $C_{17}H_{31}COOH$ | $C_{23}H_{47}COOH$ | |

6. A method as described in claim 5 wherein the alcohol is selected from the group consisting of

| | | |
|---|---|---|
| $C_5H_{11}CH_2OH$ | $C_{21}H_{43}CH_2OH$ | 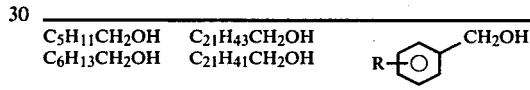 |
| $C_6H_{13}CH_2OH$ | $C_{21}H_{41}CH_2OH$ | |
| $C_7H_{15}CH_2OH$ | $C_{21}H_{39}CH_2OH$ | 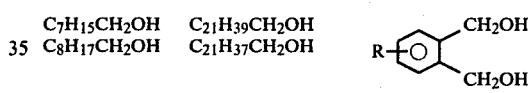 |
| $C_8H_{17}CH_2OH$ | $C_{21}H_{37}CH_2OH$ | |
| $C_9H_{19}CH_2OH$ | $C_{21}H_{35}CH_2OH$ | |
| $C_{10}H_{21}CH_2OH$ | $C_{21}H_{33}CH_2OH$ | 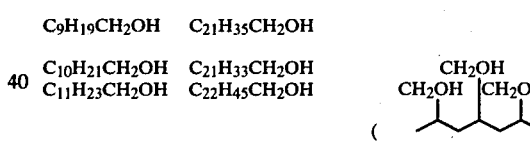 |
| $C_{11}H_{23}CH_2OH$ | $C_{22}H_{45}CH_2OH$ | |
| $C_{12}H_{25}CH_2OH$ | $C_{23}H_{47}CH_2OH$ | poly(alkyl alcohol) where n is number of repetitive units normally from about 1 to about 10,000 preferably from 10 to 1,000. |
| $C_{13}H_{27}CH_2OH$ | | |
| $C_{13}H_{25}CH_2OH$ | $HOCH_2CH_2OH$ | |
| $C_{14}H_{29}CH_2OH$ | $HOCH_2CH_2CH_2OH$ | |
| $C_{15}H_{31}CH_2OH$ | $HO(CH_2)_4OH$ | |
| $C_{15}H_{29}CH_2OH$ | $HO(CH_2)_5OH$ | |
| $C_{16}H_{35}CH_2OH$ | $HO(CH_2)_6OH$ | |
| $C_{17}H_{35}CH_2OH$ | $HO(CH_2)_7OH$ | |
| $C_{17}H_{33}CH_2OH$ | $HO(CH_2)_9OH$ | |
| $C_{17}H_{31}CH_2OH$ | $HO(CH_2)_{10}OH$ | |
| $C_{17}H_{29}CH_2OH$ | | |
| $C_{18}H_{37}CH_2OH$ | $CH_2OH$ | $HO(CH_2CH_2O)_{\overline{n}}H$ ethylene glycols wherein n is the number of repetitive units, normally from 1 to about 100, preferably 1 to about 30 |
| $C_{19}H_{39}CH_2OH$ | \| | |
| $C_{19}H_{37}CH_2OH$ | $CH_2OH$ | |
| $C_{19}H_{35}CH_2OH$ | \| | |
| $C_{19}H_{33}CH_2OH$ | $CH_2OH$ | |
| $C_{19}H_{31}CH_2OH$ | | |
| $C_{19}H_{29}CH_2OH$ | | |
| $C_{20}H_{41}CH_2OH$ | | |

7. A method as described in claim 6 wherein the hydrogenation catalyst is copper chromite.

* * * * *